United States Patent [19]

Schultz et al.

[11] Patent Number: 5,536,855

[45] Date of Patent: Jul. 16, 1996

[54] PROCESS FOR PREPARING GLYCIDYL ESTERS FOR USE IN ELECTRONICS ADHESIVES

[75] Inventors: Rose A. Schultz, Princeton; Sharon Chaplinsky, Ringoes, both of N.J.

[73] Assignee: National Starch and Chemical Investment Holding Corporation, Wilmington, Del.

[21] Appl. No.: 206,778

[22] Filed: Mar. 4, 1994

[51] Int. Cl.⁶ .................. C07D 303/36; C07D 303/14
[52] U.S. Cl. ............................................. 549/539
[58] Field of Search ................ 549/534; 546/304, 546/276, 268

[56] References Cited

U.S. PATENT DOCUMENTS

| | | | |
|---|---|---|---|
| 4,866,108 | 9/1989 | Vachon et al. | 523/428 |
| 4,975,221 | 12/1990 | Chen et al. | 252/512 |
| 5,036,154 | 7/1991 | Au | 549/531 |
| 5,218,063 | 6/1993 | Kimball | 525/531 |
| 5,250,600 | 10/1993 | Nguyen et al. | 524/377 |

FOREIGN PATENT DOCUMENTS

| | | |
|---|---|---|
| 0008111 | 2/1980 | European Pat. Off. . |
| 0008112 | 2/1980 | European Pat. Off. . |
| 0028024 | 5/1981 | European Pat. Off. . |
| 0113858 | 7/1984 | European Pat. Off. . |
| 0447360 | 9/1991 | European Pat. Off. . |
| 2602157 | 7/1976 | Germany . |
| 2654306 | 6/1977 | Germany . |
| 4232213 | 4/1993 | Germany . |
| 55-060575 | 5/1980 | Japan . |
| 58-201866 | 11/1983 | Japan . |

OTHER PUBLICATIONS

Kuhens, R.: Cycloaliphatic Glycidyl Esters. A New Class of Epoxy Resins. *Kunststoffe*, vol. 58 (1958), No. 8, pp. 565–571 (Translation provided).
Glycidyl Esters. II. Synthesis of Esters of Commercial and Pure Fatty Acids; The Journal of American Oil Chemists' Society; vol. 38; pp. 194–197 (1961), Maerker et al.
Advances in Custom-Formulated Flexible Epoxies; Adhesives Age; pp. 38–41; Jul. 1993; Hermansen, et. al.
Thallium Compounds as Catalysts for Transesterifications and Ester Exchange Reactions; Helvetica Chimica Acta—vol. 60, (1977) p. 1845 (Abstract only); Zondler, et. al.
Glycidyl Esters. I. Method of Preparation and Study of Some Reaction Variables; JOC vol. 26; Aug. 1961; pp. 2681–2688; Maerker, et. al.
Dimer Acids; Encyclopedia of Chemical Technology, 4th addition, vol. 8; pp. 223–234 (Date not available). Kirk–Othmer.
Pyrrolizidine Alkaloid Analogues, Preparation of Semisynthetic Esters of Retronecine; J. C. S. Perkins 1, 1977, pp. 538–544; Hoskins, et. al.
Simple Method for the Esterification of Carboxylic Acids; Chem. Int. Ed. Engl. 17 (1978) No. 7; p. 522–524; Neises, et. al.
Macromolecules, vol. 26. No. 12, 1993, p. 2996; Gangadhara, et. al.
Synthesis of Glycidol Esters and Mono/Di-Acylglycerols from Glycidol; Chemistry and Physics of Lipids, 36 (1985) p. 329–332; Lok et al.
Esterification of Acids; Adv. Organic Chem., 3rd Ed. 1985, p. 348–354; March.
Glycidyl Esters of Aliphatic Acids; JOC 1943; p. 550–556; Kester, et. al.
4–Dialkylaminopyridines as Highly Active Acylation Catalysts; Angew. Chem. Ind. Ed. Engl. 17, (1978) p. 569–583, Höfle, et. al. pp. 569, 570, 573–583.
Carbodiimide Chemistry:Recent Advances; Chem. Rev. 1981, 81, 589–636 Williams, et. al.
Direct Room Temperature Esterification of Carboxylic Acids; Alfred Hassner, et. al. pp. 4475–4478 (Date not available).
Unichema International, PRIPOL Product Data Sheet, May 1988; 3 page data sheet.
Henkel, Empol Dimer and Polybasic Acids Data Sheet, pp. 1–11 (date not available).

*Primary Examiner*—Robert W. Ramsuer
*Assistant Examiner*—Laura R. Cross
*Attorney, Agent, or Firm*—Jane E. Gennaro

[57] ABSTRACT

Glycidyl esters are prepared to have low chlorine, chloride, sodium and potassium contamination and a thixotropic index greater than 3.0 by a process that comprises reacting carboxylic mono- or dimer acids with glycidyl alcohols in a molar ratio of 1 to (0.9–4.0) using carbodiimide as the acylating agent and a pyridine-type catalyst. The pyridine-type catalyst is removed by strongly acidic ion exchange resin.

6 Claims, No Drawings

PROCESS FOR PREPARING GLYCIDYL ESTERS FOR USE IN ELECTRONICS ADHESIVES

FIELD OF THE INVENTION

This invention pertains to flexible epoxy compounds suitable for use in microelectronics applications and a process for their preparation.

BACKGROUND OF THE INVENTION

Epoxy compounds are widely preferred as die-attach, bonding and encapsulating adhesives in the microelectronics industry due to their good adhesion to a broad spectrum of materials. Although conventional epoxy compounds are inherently rigid and brittle, making them susceptible to the stress of thermal cycling in manufacturing procedures and potentially leading to adhesive failure or fracture of the die or chip, recent advances in formulating epoxy adhesives have resulted in epoxies that are flexible and resilient. According to the principles outlined in "Advances in Custom-Formulated Flexible Epoxies", by R. D. Hermansen and S. E. Lau, *Adhesives Age*, 38, July 1993, flexibility can be obtained in a polymer by the absence of ring structures, low levels of crosslinking, and free rotation about polymeric bonds. Carbon-carbon double bonds adjacent to carbon-carbon single bonds, and ester and ether groups enhance free rotation.

Glycidyl esters, which are the reaction products of glycidyl alcohols and mono- or dimer carboxylic acids, are flexible and particularly suitable for use as the epoxy base in microelectronics adhesives. The prior art has looked at several methods to prepare glycidyl esters, but these methods are not without disadvantages when the product will be used in electronics devices.

For example, the synthesis of these compounds can be accomplished by glycidization of carboxylic acids (G. Maerker; *J. Org. Chem.*, 26, 2681 (1961)), or carboxylic acid salts (G. Maerker; *J. Am. Oil chem. Soc.*, 38, 194 (1961)) with epichlorohydrin in the presence of sodium hydroxide, or by glycidization of carboxylic acid chlorides with glycidol (E. B. Kester; *J. Org. Chem.*, 550 (1943)). These methods leave high levels of residual chlorine, chloride and alkali metal ions, which, when used in adhesives for microbonding in electronics devices, tend to promote corrosion of electrical leads in the vicinity of the adhesive.

Glycidyl esters have also been prepared by the transesterification of carboxylic acids using an alkali metal halide (Japanese patent 55127389), such as sodium bromide, or thallium compounds (*Helvetica Chimica Acta*, 60, 1845 (1977)), but halide ions are potentially corrosive in microelectronics applications, and thallium compounds are known to be extremely toxic (Merck Index).

In still another method, glycidol can be reacted with an acid anhydride; however, the result is that one molecule of acid is formed as a by-product for every molecule of glycidyl ester (M. Lok; *Chem. and Phys. of Lipids*, 36, 329 (1985)).

U.S. Pat. No. 5,036,154 describes the preparation of glycidyl esters by the oxidation of allyl esters employing hydrogen peroxide with salts of tungstic acid and phosphoric acid, and a phase transfer catalyst. This method requires a long reaction time, and residual phase transfer catalyst can be difficult to remove and can cause premature polymerization.

A dehydration system using N,N'-carbonyldiimidazole (*J. C. S. Perkin* I, 538 (1977)) is known to effect ester formation from carboxylic acids and alcohols, but the imidazole by-product will react with oxiranes at room temperature.

Carbodiimides have been described as acylating agents for esterification (*Chem. Rev.*, 81, 589 (1981)); they have not, however, been considered to be very useful for this purpose because side products formed from the rearrangement of the 0-acyl isourea intermediate reduce the yield of the desired product. If catalytic quantities of a pyridine derivative are used in the reaction, the yield of ester can be enhanced.

In Japanese patent application 05 59,031, a carbodiimide reagent and pyridine-type catalyst are used to condense glycidol with a carboxylic acid to afford a glycidyl ester. This method is specific to amino acid containing compounds used for their liquid crystal properties, which are known to impart rigidity and stiffness to a system. These compounds can be recovered as precipitated crystals. Flexible epoxy compounds, in contrast, generally take the form of oil, and are not easily recovered from the reaction medium. Furthermore, many of these flexible epoxies are derived from dimer acids and other fatty acids and tend to form severe emulsions when an aqueous extraction is performed to isolate the product. The emulsions also prevent the complete removal of the pyridine-type catalyst, which if not removed, over time will react with the epoxy, increasing the viscosity, decreasing the oxirane content, and sometimes causing the product to form into a gel.

Another requirement for an electronics adhesive is that the thixotropic index be high and remain stable over a prolonged period (usually about 24 hours). The thixotropic index is the ratio between the viscosity of the adhesive at high shear and that at low shear. In many microbonding operations, the adhesive is delivered by syringe under shear. The higher the thixotropic index of the adhesive, the cleaner its delivery from syringe to substrate because the viscosity of the adhesive increases immediately upon dispensing as the shear is reduced. Clearly, the cleaner the delivery, the faster and more economical the microbonding operation can be. Adhesives used in microelectronics applications are typically loaded at levels up to 90% by weight with electrically or thermally conductive fillers, such as, silver, gold, copper, nickel, or silica. If any residual acid is left in the glycidyl ester, even at low levels, the acid has been found to cause a significant decrease in the thixotropic index of an adhesive containing a filler, particularly, for example, silver, in just 24 hours.

Thus, despite the fact that flexible epoxies are known and available, none meet all the requirements for a superior epoxy adhesive for use in microelectronics applications, namely, a high oxirane content, low ionic contamination, retention of a stable and workable viscosity, and when loaded with electrically or thermally conductive fillers a high, stable thixotropic index.

SUMMARY OF THE INVENTION

This invention is a glycidyl ester suitable for use in microelectronics applications that has less than 100 ppm contamination by chlorine, chloride, sodium, potassium, or other elemental, salt, or ionic impurities, a residual acid number of 15,000 g/equivalent or greater and a thixotropic index that holds stable at greater than 3.0, preferably greater than 3.5, when loaded with conductive fillers.

In another embodiment, this invention is a process for the synthesis of a glycidyl ester from the reaction of a flexible carboxylic acid with glycidol, one or more glycidol derivatives, or a combination of glycidol and its derivatives in the presence of a carbodiimide as the acylating agent and a pyridine-type catalyst. Contamination is avoided by employing a process that does not use epichlorohydrin or alkali metal. The process comprises reacting the acid and alcohol at a molar ratio of acid to alcohol of 1 to (0.9 to 4) to minimize the residual acid content, and effecting nearly complete removal of any residual pyridine-type catalyst. The reduction of the acid level assures recovery of a product with a stable thixotropic index, and the removal of the pyridine-type catalyst assures the recovery of a product with a sufficiently low workable viscosity and good stability.

When the reaction between the carboxylic acid and glycidyl alcohol is complete, the organic solution is filtered to remove any urea by-product. Although it could be expected that a strong acid would destroy oxirane content in the product, it has been found that treatment with a strongly acidic cation exchange resin, in which the pKa of the acid is equal to or less than 2.0 relative to water, preferably less than 2.0, at a temperature below 25° C., preferably between 0°–15° C., is effective to remove the pyridine-type catalyst without appreciable loss in epoxy product. Minimal amounts of water and methanol are added to provide sufficient contact between the ion exchange resin and the organic solution. A small amount of 50% aqueous acetic acid is used to quench any remaining carbodiimide. The pH is then adjusted to neutral with a suitable salt, and the solution filtered to remove any residual urea. The water and solvent are then removed in vacuo and the glycidyl ester product redissolved in an organic solvent, such as heptane or toluene. The solution is cooled for several hours and if any residual urea crystallizes, it is filtered out. The solvent and remaining glycidol are removed under reduced pressure isolating the glycidyl ester as an oil in about 90–97% yield.

DETAILED DESCRIPTION OF THE INVENTION

The starting carboxylic acids can be any known flexible monocarboxylic or dicarboxylic acids with at least four carbon atoms, or mixtures of flexible mono- and dimer acids. As discussed above, flexibility fairly can be predicted by choosing acids that have minimum ring structures, low levels of crosslinking, and free rotation about polymeric bonds due to the presence of a preponderance of carbon-carbon single bonds, and ester and ether groups.

Suitable acids can be represented by the formula X—R—X', in which X is hydrogen or carboxyl group; X' is a carboxyl group; and R is $C_1$–$C_{66}$ alkyl chain with or without one or more carbon-carbon double bonds, $C_5$–$C_6$ cycloaliphatic or cycloaromatic groups in the chain, or a polymeric radical derived from polyethers, polyamides, polybutadienes, polyacrylonitriles, or poly(cobutadiene-acrylonitriles).

The preferred acids are dicarboxylic acids, such as, dimers of oleic acid, linoleic acid, or tall oil fatty acids. Commercially available dimer acids may be obtained from Unichema under the tradename "Pripol", or from Henkel under the tradename "Empol". Monocarboxylic acids, such as sebacic acid, stearic acid, and ricinoleic acid, may also be used, although preferably they will be used in combination with dimer acids in amounts not to exceed 50–70% by weight of the total acid content.

Examples of suitable polymeric acids are carboxy-terminated-cobutadiene acrylonitrile, or polyether diacids derived by oxidation of polyethylene glycol (for example, poly(tetramethylene glycol)diacid), or polyethers terminated with anhydrides to provide terminal acid groups. Examples of such acids can be found in U.S. Pat. No. 4,975,221, and in *Macromolecules*, Vol. 26, No. 12, 2996 (1993), incorporated herein.

The glycidyl alcohol reacted with the carboxylic acid is glycidol, or one or more of its derivatives, or a combination of glycidol with one or more of its derivatives. The derivative can be the R- or S- enantiomer, or the racemic mixture. Suitable derivatives are represented by the structure:

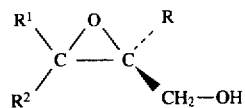

in which R, $R^1$ and $R^2$ independently can be hydrogen, $C_1$–$C_{26}$ alkyl (preferably methyl, ethyl, or propyl), $C_1$–$C_5$ alkyl ether, $C_3$–$C_6$ cycloaliphatic, aromatic, or aromatic substituted with methyl, ethyl, halide, or nitro groups; or $R^1$ and $R^2$ together can be $C_5$–$C_6$ cycloaliphatic or heterocycloaliphatic with O, N, S, or P. The preferred derivatives are 2-methylglycidol and 3-phenylglycidol. The more preferred reactant is racemic glycidol.

The amount of glycidol or glycidol-derivative to be reacted with the flexible carboxylic acid will range from 0.90 to 4.00 molar equivalents per carboxyl group, preferably will be 1.0 to 2.0 molar equivalents, and more preferably will be 1.02 to 1.5 molar equivalents per carboxyl group.

The carbodiimide acylating agent is represented by the structure:

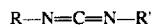

in which R and R' independently can be $C_3$–$C_{16}$ alkyl, $C_5$–$C_6$ cycloaliphatic, phenyl group, or tolyl group; or can be $C_3$–$C_{16}$ alkyl, $C_5$–$C_6$ cycloaliphatic, phenyl group, or tolyl group bound to a polymeric chain. In practice, the carbodiimide can be any of the commonly available reagents, for example, 1,3-diisopropyl carbodiimide; 1,3-dicyclohexyl carbodiimide; and 2,2',6,6'-tetraisopropyl-diphenyl carbodiimide, sold under the tradename Stabaxol I, or its polymeric version, Stabaxol P, by Rhein Chemie. Another example of a commercially available polymeric carbodiimide is that sold under the tradename UCARLINK XL29SE from Union Carbide. The preferred agent is 1,3-dicyclohexyl carbodiimide.

Inasmuch as the glycidyl alcohol is used in excess in the reaction, the conversion is dependent of the amount of carbodiimide used. The exact amount of carbodiimide to be used will be chosen to result in a minimum of residual carboxylic acid. In general, the carbodiimide typically will be employed at levels of 0.9 to 1.1 molar equivalents, preferably at 0.98 to 1.02 molar equivalents, per carboxyl group. As will be shown in the examples, the less residual acid in the adhesive, the more stable the thixotropic index.

The pyridine-type catalysts will have one of the structures:

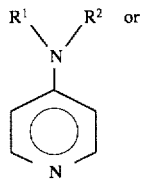

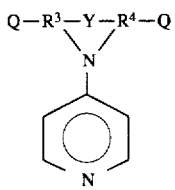

$$Q-R^3-Y-R^4-Q \quad \text{II.}$$

in which $R^1$ and $R^2$ are independently $C_1$–$C_4$ alkyl; or $R^1$ and $R^2$ together are C-$[N(CH_3)_2]_2$, cyclic $(CH_2)_4$, or heterocycloaliphatic $(CH_2)_2$ to $(CH_2)_4$ containing O, N, or S in any position except adjacent to the nitrogen bound to the pyridine ring (such as in morpholine, piperazine, thiazine, oxazole, oxazoline, thiazole, and thiazoline), and $R^3$ and $R^4$ are methylene or methine groups, Y is O, N, S, P, $C_1$–$C_4$ alkyl, and Q is the polymerized product of vinyl comonomers or homopolymer. The preferred pyridine-type catalysts are the 4-di-$(C_1$–$C_4)$alkylaminopyridines, the more preferred is 4-dimethylaminopyridine.

The pyridine-type catalyst will be used in the amounts of 0.10 to 5 molar equivalents, preferably 0.5 to 1.5 molar equivalents, based on 100 molar equivalents of carboxylic acid groups.

The reaction between the acid and glycidol, or glycidol-derivative, in the presence of the carbodiimide and pyridine-type catalyst, will be conducted at a temperature from $-20°$ to $100°$ C., preferably from $-10°$ to $25°$ C. This temperature range has been found to limit the amount of glycidol and glycidyl ester that reacts with or is polymerized by the pyridine-type catalyst to give an undesired byproduct. The reaction can be conducted under pressure, but pressure is not necessary to effect the esterification.

Suitable solvents in which the reaction may be conducted include chlorinated aliphatics, such as, methylene chloride, dichloroethane; amides, such as, dimethyl formamide, dimethyl acetamide and N-methylpyrrolidinone; aromatics, such as, benzene, toluene, chlorobenzene; ketones, such as, acetone, methyl ethyl ketone, methyl isobutyl ketone; ethers, such as, diethyl ether, tetrahydrofuran; aliphatic hydrocarbons, such as hexane, heptane, and the like. The solvents are chosen to assure the solubility of the reactants and product in the solvent. The preferred solvents are dichloroethane, toluene, and heptane. The concentration of reactants in the solvent can range from 5–85% by weight, preferably 20–50% by weight. The limiting factor in determining concentration will be the ability to obtain a workable viscosity of the reaction solution.

After the reaction is complete, as determined by the appearance of an ester IR band and disappearance of the carbodiimide IR band, the product is isolated using a non-aqueous extraction. Derived, usually, from fatty acid materials, the flexible epoxy esters prepared by this process will develop severe emulsions if subjected to an aqueous extraction. The emulsions lead to low yield and insufficient removal of the pyridine-type catalyst, which results in gelling (crosslinking) of the product.

To circumvent the emulsification problem, the organic layer, after filtration to remove the urea byproduct, is treated with a strongly acidic cation exchange resin in the H$^+$ form, having a pKa equal to or less than 2.0, preferably less than 2.0, at a level from 1–100 molar equivalents, preferably 10 molar equivalents, based on the pyridine-type catalyst. An example of a suitable strong acid is sulfonic acid. One preferred cation exchange resin commercially available is Amberlyst® 15, a product of Rohm and Haas, obtainable from Aldrich Chemical Company. Very small amounts of water or lower alcohol, such as, methanol or isopropanol, are used to provide sufficient contact between the ion exchange resin and the organic layer. The amounts of water or alcohol will not exceed 10 parts per 100 parts by volume of the reaction solution. The resin and any additional urea byproduct are removed by filtration. In addition to quenching the pyridine-type catalyst, the ion exchange treatment also serves to quench residual carbodiimide. If any residual carbodiimide remains after treatment with the ion exchange resin, a small amount of 50% aqueous acetic acid, preferably less than 5 parts per 100 parts by volume of the reaction mixture, is used to finish quenching the carbodiimide, and the acid then neutralized with a suitable salt, such as solid $NaHCO_3$, $KHCO_3$, or $Na_2HPO_4$. The solution is then filtered, and if sufficient salt was added, the aqueous layer can be drawn off. Otherwise, the water can be removed with the solvent by distillation under vacuum. The oily product is redissolved in an organic solvent, such as heptane or toluene, cooled for several hours, and filtered to remove any crystallized urea. The solvent and remaining glycidyl alcohol are removed under reduced pressure to leave the glycidyl ester as an oil in about 90–97% yield.

EXAMPLES

Example 1

Preparation of the Diglycidyl Ester of Glutaric Acid

This example shows the preparation of a low formula weight glycidyl ester with a flexible aliphatic chain that is useful as a viscosity reducer or reactive diluent in adhesives.

A multi-necked round bottom flask equipped with mechanical stirrer, thermometer, $N_2$ purge and slow-addition funnel was charged with 10.00 g (0.0756 moles) of glutaric acid, 22.40 g (0.3024 moles) glycidol, 60 ml of methylene chloride and a catalytic amount (0.15 g, 1.23 millimoles) of 4-dimethylaminopyridine. The reaction was cooled to 0°–5° C. and to this was added a solution of 31.18 g (0.1512 moles) 1,3-dicyclohexylcarbodiimide in 60 ml of methylene chloride over a period of 45 minutes. The reaction was then allowed to reach ambient temperature and held overnight. The reaction was determined to be complete by IR (appearance of ester at 1735 cm$^{-1}$) and the disappearance of the 1,3-dicyclohexylcarbodiimide (2120 cm$^{-1}$). The reaction mixture was filtered to remove the 1,3-dicyclohexylurea byproduct, and washed sequentially with 5% acetic acid (2×50 ml), saturated sodium bicarbonate (50 ml), and water (3×50 ml) The product solution was then dried over magnesium sulfate. The methylene chloride was removed under reduced pressure using a rotory evaporator. Residual solvent and any remaining glycidol were subsequently removed using a kugelrohr apparatus (80° C./0.1–0.2 mmHg vacuum).

The product was isolated as an oil (12.2 g, 58% yield) and was characterized as follows:

IR spectrum: ester at 1735 cm$^{-1}$ $^1$H NMR spectrum: $\delta 1.8$–2.2, t(2H); $\delta 2.25$–2.95, m(8H); $\delta 3.1$–3.35, m(2H); $\delta 3.4$–4.6, m(4H)

Epoxy equivalent weight: 180 (theoretical=122)

Residual Acid titration: acid number=27,747 g/equivalent

Examples 2 to 4 show that an aqueous work-up does not effectively remove all the pyridine-type catalyst and results in excessive cross-linking or gelling of the product.

Example 2

Preparation of the Diglycidyl Ester of Dimer Acid (Pripol® 1009)

A multi-necked round bottom flask equipped with mechanical stirrer, thermometer, $N_2$ purge and slow-addition funnel was charged with 50.00 g (0.0.0864 moles) of Pripol® dimer acid (Unichema), 25.60 g (0.3455 moles) glycidol, 500 ml of toluene and a catalytic amount (0.75 g, 6.14 millimoles) of 4-dimethylaminopyridine. The reaction was cooled to 0°–5° C. and a solution of 33.85 g (0.1643 moles) 1,3-dicyclohexylcarbodiimide in 250 ml toluene was added over a period of 45 minutes. The reaction was allowed to reach ambient temperature and held for 2 hours. The reaction was determined to be complete by IR, appearance of ester at 1735 cm$^{-1}$, and the disappearance of the 1,3-dicyclohexylcarbodiimide, 2120 cm$^{-1}$. The reaction mixture was filtered to remove the 1,3-dicyclohexylurea byproduct. The product solution was then washed with 0.1N hydrochloric acid (2×100 ml), followed by 5% sodium carbonate (1×200 ml), and dried over magnesium sulfate. Toluene was removed under reduced pressure using a rotory evaporator, and residual solvent and glycidol were subsequently removed using a kugelrohr apparatus (80° C./0.1–0.2 mmHg vacuum).

The product was isolated as a gel (10.40 g, 86% yield) and was characterized as follows:

IR spectrum: ester at 1735 cm$^{-1}$

The product cross-linked while on the kugelrohr apparatus and could not be characterized further.

Example 3

Preparation of the Diglycidyl ester of Dimer Acid (Pripol® 1009)

The reaction was carried out as described in Example 2 above. The product solution was filtered to remove the 1,3-dicyclohexylurea byproduct. To the product solution was then added 20 ml of water, 20 ml of methanol and 34 ml of Amberlyst® 15 (H$^+$ form). The product solution was stirred for 30 minutes and then filtered to remove the Amberlyst® resin. The solvent was removed using a rotory evaporator under reduced pressure. Residual solvent and any remaining glycidol were subsequently removed using a kugelrohr apparatus (80° C./0.01–0.02 mmHg vacuum).

The product was isolated as an oil (57.19 g, 94% yield) and was characterized as follows:

IR spectrum: ester at 1735 cm$^{-1}$

Epoxy equivalent weight: 408 (theoretical=318)

Residual Acid titration: acid number=12,563 g/equivalent

Example 4

Preparation of the Diglycidyl Ester of Dimer Acid (Empol® 1024)

The reaction was carried out as described in Example 2 at 25× the scale using distilled glycidol with the addition that acetic acid was used to help quench the carbodiimide. At the completion of the 2 hour hold some unreacted 1,3-dicyclohexylcarbodiimide (2120 cm$^{-1}$) was present. The product solution was then filtered at 0°–5° C. to remove the 1,3-dicyclohexylurea byproduct. To the product solution was then added 50 ml of water, 50 ml of methanol and 96 ml of Amberlyst® 15 (H$^+$ form). The product solution was stirred for 30 minutes at 10°–15° C. and then filtered to remove the Amberlyst® resin. Acetic acid (20%) (5 ml) was added to the solution with stirring to quench any residual 1,3-dicyclohexylcarbodiimide. After 30 minutes the reaction was examined by IR for the absence of the 1,3-dicyclohexylcarbodiimide (2120 cm$^{-1}$). Sodium bicarbonate was then added until the solution reached pH 7. The reaction was filtered and the solvent removed using a rotory evaporator under reduced pressure. The product was then dissolved in 1 volume of toluene and stored overnight in a freezer. The solution was filtered cold and the solvent removed using a rotory evaporator under reduced pressure. Residual solvent and glycidol were subsequently removed using a kugelrohr apparatus (80° C./0.1–0.2 mmHg vacuum).

The product was isolated as an oil (248.63 g, 92% yield) and was characterized as follows:

IR spectrum: ester at 1735 cm$^{-1}$

Epoxy equivalent weight: 353 (theoretical=318)

Residual Acid titration: acid number=1,439,000 g/equivalent

TABLE 1

| Comparison of Results Using Different Work Up Procedures | | |
|---|---|---|
| Example # | Yield % | Viscosity |
| 2 (aq. ext.) | 86 | gelled |
| 3 (ion exch.) | 94 | 728 cps |
| 4 (ion exch.) | 92 | 396 cps |

Examples 5 through 8 show the effect of residual acid levels on the stability of the thixotropic index of glycidyl ester formulated with 80% by weight silver metal flakes.

Example 5

Preparation of the Diglycidyl Ester of Dimer Acid (Empol® 1024)

A multi-necked round bottom flask equipped with mechanical stirrer, thermometer, $N_2$ purge and slow-addition funnel was charged with 50.00 g (0.0868 moles) of Empol® 1024 dimer acid (Henkel), 19.29 g (0.2604 moles) glycidol, 200 ml of toluene and a catalytic amount (0.212 g, 0.0017 moles) of 4-dimethylaminopyridine. The reaction was cooled to 0°–5° C. and to this was added a solution of 35.05 g (0.1701 moles) 1,3-dicylcohexylcarbodiimide in 100 ml of toluene over a period of one hour. After carbodiimide addition was complete, the reaction was held at 0°–5° C. for 15 minutes and then at 10°–15° C. for two hours. The reaction was determined to be complete by IR, appearance of ester at 1735 cm$^{-1}$, and the disappearance of the 1,3-dicyclohexylcarbodiimide at 2120 cm$^{-1}$. The product solution was cooled to 0°–5° C., held for 15 minutes, and filtered to remove the 1,3-dicylcohexylureabyproduct. The product solution was then chilled to 10°–15° C. with stirring, and a solution of 20 ml of 50:50 water:methanol and 34 ml of Amberlyst® 15 (H$^+$ form) was added. The reaction was filtered and the solvent removed using a rotory evaporator under reduced pressure. The product was dissolved in 30 ml toluene and stored overnight in a freezer. The solution was then filtered cold, and the solvent removed using a rotory evaporator under reduced pressure. Residual solvent and glycidol were subsequently removed using a kugelrohr apparatus (80° C./0.1–0.2 mmHg vacuum). The product was isolated as an oil (46.48 g, 78% yield) and was characterized as follows:

IR spectrum: ester at 1735 cm$^{-1}$

Epoxy equivalent weight: 359 (theoretical=344)

Residual Acid titration: acid number=7,255 g/equivalent

Example 6

Preparation of the Diglycidyl Ester of Dimer Acid (Empol® 1024) with Lower Residual Acid Values In this example, additional reagents are added to consume more residual acid. To 15 g of product prepared in Example 6 above was added 0.51 g (6.532 millimoles) glycidol, a catalytic amount (0.005 g, 6.53 millimoles) of 4-dimethylaminopyridine and 50 ml toluene. The reaction was cooled to 0°–5° C. and a solution of 1.00 g (0.0048 moles) dicyclohexylcarbodiimide in 10 ml of toluene was added over 15 minutes. The reaction was held at 0°–5° C. for 15 minutes, then at 10°–15° C. for 1 hour. The product solution was cooled to 0°–5° C., held for 15 minutes, and then filtered cold to remove the 1,3-dicyclohexylurea byproduct. The product solution was chilled to 10°–15° C. with stirring and a solution of 4 ml of 50:50 water:methanol and 1 ml of Amberlyst® 15 (H$^+$ form) was added. The reaction was filtered, cooled to 10°–15° C. with stirring, and 1.5 ml of 30% acetic acid in water was added. After 30 minutes the reaction was examined by IR for the absence of the 1,3-dicyclohexylcarbodiimide (2120 cm$^{-1}$) and determined to be complete. Sodium bicarbonate was added until the solution reached a pH of 7. The reaction mixture was dried over magnesium sulfate, filtered, and the solvent was removed using a rotory evaporator under reduced pressure. Residual solvent and glycidol were subsequently removed using a kugelrohr apparatus (80° C./0.1–0.2 15 mmHg vacuum). The product was isolated as an oil (10.9 g, 73% yield) and was characterized as follows:

IR spectrum: ester at 1735 cm$^{-1}$

Epoxy equivalent weight: 357 (theoretical=344)

Residual Acid titration: acid number=268,857 g/equivalent

The following examples 7 and 8 show that the stability of the thixotropic index is a function of the residual acid content and not the starting dimer acid.

Example 7

Preparation of the Diglycidyl Ester of Dimer Acid (Pripol® 1009)

The reaction was carried out as described in Example 5, with the exception that Pripol® 1009 was used as the dimer acid and the chemistry adjusted accordingly. The product was isolated as an oil (55.83g, 92% yield) and was characterized as follows:

IR spectrum: ester at 1735 cm$^{-1}$

Epoxy equivalent weight: 374 (theoretical=318)

Residual Acid titration: acid number=8,149 g/equivalent

Example 8

Preparation of the Diglycidyl Ester of Dimer Acid (Pripol® 1009) with Lower Residual Acid The product (20.00 g) of Example 7 above was treated with additional reagents as described in Example 6 above. The product was isolated as an oil (13.94 g, 69% yield) and was characterized as follows:

IR spectrum: ester at 1735 cm$^{-1}$

Epoxy equivalent weight: 353 (theoretical=318)

Residual Acid titration: acid number=106,905 g/equivalent

The results are summarized in the following table. Results for the chlorine content only are reported, although it will be recognized that reduction of chlorine content also indicates reduction of other chemical elemental or ionic contaminants resulting from the synthesis of the materials.

TABLE 2

Comparison of Residual Acid Level and Thixotropic Index of Glycidyl Esters Formulated with 80% by Weight of Ag

| Example # | Residual Acid g/equiv | Thixotropic Index Day 0 | Thixotropic Index Day 1 | Thixotropic Index Day 5 | Chlorine PPM |
|---|---|---|---|---|---|
| EPON 871* | 251,794 | 4.1 | 3.8 | 3.8 | 13449.0 |
| 5 | 7,255 | 4.0 | 2.4 | 2.8 | ND** |
| 6 | 268,857 | 4.9 | 4.8 | 5.1 | ND** |
| 7 | 8,149 | 3.6 | 2.5 | 2.6 | 50.5 |
| 8 | 106,905 | 5.2 | 4.8 | 4.9 | ND** |

*A commercially available epoxy adhesive.
**Not detectable.

Examples 9 through 11 show that suitable glycidyl esters can be prepared from other flexible polymeric acids and glycidol.

Example 9

Preparation of Diglycidyl Ester of Carboxy Terminated Butadiene-Co-Acrylonitrile (Hycar® 1300×13)

A multi-necked round bottom flask equipped with mechanical stirrer, thermometer, N$_2$ purge and slow-addition funnel was charged with 10.00 g (0.0034 moles) of carboxy terminated butadiene-co-acrylonitrile (Hycar 1300×13) (a product of B. F. Goodrich Co.), 0.78 g (0.010 moles) glycidol, 150 ml of toluene, and a catalytic amount (0.008 g, 0.0067 moles) of 4-dimethylaminopyridine. The reaction was cooled to 0°–5° C. and to this was added a solution of 1.45 g (0.007 moles) 1,3-dicyclohexylcarbodiimide in 50 ml of toluene over a period of 1 hour. After addition of the carbodiimide, the reaction was held at 0°–5° C. for 15 minutes, then at 10°–15° C. for two hours. The reaction was determined to be complete by IR, appearance of ester at 1735 cm$^{-1}$, and the disappearance of most of the 1,3-dicarboxylcarbodiimide at 2120 cm$^{-1}$. The product solution was cooled to 0°–5° C., held for 15 minutes, and then filtered to remove the 1,3-dicyclohexylurea byproduct. The product solution was chilled to 10°–15° C. with stirring and a solution of 4 ml of 50:50 water:methanol and 0.8 g of Amberlyst® 15 (H$^+$ form) was added. The product solution was stirred for 30 minutes at 10°–15° C. and then filtered to remove the Amberlyst® resin. Acetic acid, 50%, (4 ml) was added with stirring. After 30 minutes the reaction was examined by IR for the absence of the 1,3-dicyclohexylcarbodiimide and determined to be complete. Sodium bicarbonate was added to the reaction until the pH reached 7. The solution was filtered and the solvent removed using a rotory evaporator under reduced pressure. The product was dissolved in 30 ml toluene/heptane and stored overnight in a freezer. The solution was then filtered cold, and the solvent removed using a rotory evaporator under reduced pressure. Residual solvent and glycidol were subsequently removed using a kugelrohr apparatus (80° C./0.1–0.2 mmHg vacuum). The product was isolated as an oil (8.6 g, 82% yield) and was characterized as follows:

IR spectrum: ester at 1735 cm$^{-1}$

Epoxy equivalent weight: 1988 (theoretical=1547)

Residual Acid titration: acid number=69,569 g/equivalent

Example 10

Preparation of Diglycidyl Ester of Carboxy-terminated (Poly Tetramethylene Glycol)

This reaction was carried out as described in Example 9 above using 10 g (0.0086 moles) of carboxy-terminated-poly(tetramethylene glycol) (CTPE) acid #=1166 mg/meq [described in U.S. Pat. No. 4,975,221 Example I] and adjusting the chemistry accordingly.

The product was isolated as an oil (8.7 g, 83% yield) and was characterized as follows:

IR spectrum: ester at 1735 cm$^{-1}$

Epoxy equivalent weight: 1484 (theoretical=1222)

Residual Acid titration: acid number=75,413 g/equivalent

The CTPE was made as follows: Poly(tetramethylene glycol) [Terathane® 2000 from DuPont, MW app. 1000] (990.2 g), succinic anhydride (200.2 g) in 150 ml toluene were charged to a reaction flask and heated to reflux for 4 hours at 160° C. When the reaction was complete the volatiles were removed on a rotary evaporator under high vacuum. The yield was 99% of a clear, viscous resin, with a neutralization equivalent of 1166 g/eq (theoretical NE=1100).

Example 11

Preparation of Diglycidyl Ester of Carboxy-terminated Poly (Propylene Glycol)

This reaction was carried out as described in Example 9 above using 10 g (0.0063 moles) of carboxy-terminated poly (propylene glycol) (CTPP) acid #=1584 mg/meq [described in U.S. Pat. No. 4,975,221 Example II] and adjusting the chemistry accordingly.

The product was isolated as an oil (8.7 g, 83% yield) and was characterized as follows:

IR spectrum: ester at 1735 cm$^{-1}$

Epoxy equivalent weight: 1576 (theoretical=1640)

Residual Acid titration: acid number=60,338 g/equivalent

The CTPP was made as follows: Polypropylene glycol, molecular weight 2000, (813.04 g), succinic anhydride (80.08 g), 5 ml triethylamine, in 600 ml toluene were charged to a reaction flask and refluxed at approximately 120° C. for 6 hours. The reaction mixture was cooled to room temperature and washed 3 times with distilled water. The toluene was removed under high vacuum, and the product isolated. The neutralization equivalent was determined to be 1584 g/eq (theoretical NE=1091).

Epoxy Equivalent Weight: The epoxy equivalent weight was determined by dissolving the compound in glacial acetic acid followed by titration with standardized HBr/acetic acid (appr. 0.1N) to the violet/green transition of crystal violet indicator. The data is represented as equivalent weight for the epoxide products.

Acid Titration: The acid content was determined by dissolving the compound in acetone and titrating with 0.1N NaOH to the clear/pink transition of phenolphthalein indicator. The data is represented as grams per equivalent —COOH for residual acid in the epoxide products.

Chlorine Content: The hydrolyzable chlorine content was determined by digesting the compound in 3N KOH/ethanol in dioxane solvent at reflux for 30 minutes. The digested sample was then acidified and titrated with standardized AgNO$_3$ (appr. 0.005N) using a potentiometric electrode.

Viscosity: The viscosity was determined using a Brookfield cone-n-plate viscometer at multiple spindle speeds at 25° C. For the viscosity of the product epoxide compounds the viscosity is reported as an average of these readings. For the Ag filled epoxide formulations the thixotropic index is obtained by acquiring the viscosity at two different spindle speeds and is reported as the ratio of the two viscosity readings.

The following example is a die-attach formulation using the glycidyl ester of Example 6 and shows the flexibility imparted by the use of these compounds.

Example 12

Die Attach Adhesives

A die attach adhesive was prepared by blending the ingredients:

7.0 g diglycidyl ester of dimer acid (as described in Example 6 above)

3.0g diglycidyl ether of bisphenol F 2.0g Jeffamine D2000 (a product of Huntsman Chemical Corp.)

0.4g dicyandiamide 0.2g of a proprietary solid imidazole catalyst.

After sufficient mixing to provide a well-blended material, Ag metal flake was then mixed in to achieve an 82% by weight silver loading. The adhesive formulation was then degassed and used to adhere a silicon chip to a metal lead 25 frame. The bond was achieved by curing at 175° C. for 2 hours. The tensile modulus of the cured adhesive was measured to be 187,000 psi.

By comparison, Ablebond®84-1LMI, a typical die attach adhesive which does not contain the dimer acid glycidyl ester, has a tensile modulus of >900,000 psi.

We claim:

1. A process for the synthesis of a flexible glycidyl ester characterized as having less than 100 ppm chlorine, chloride, potassium or sodium contamination, a stable thixotropic index greater than 3.0, and a residual acid number >15,000 g/equivalent, that comprises (A) reacting (a) one or more flexible dicarboxylic or carboxylic acids represented by the structure X—R—X', in which X is hydrogen or carboxyl group;

X' is a carboxyl group; and

R is $C_2$–$C_{66}$ alkyl chain when X and X' are carboxyl groups and $C_3$–$C_{66}$ alkyl chain when X is hydrogen, with or without one or more carbon-carbon double bonds, $C_5$–$C_6$ cycloalkyl or aromatic groups in the chain, or a polymeric radical derived from polyethers, polyamides, polybutadienes, polyacrylonitriles, or poly(cobutadiene-acrylonitriles), present in an amount of 1 mole equivalent of carboxyl groups and (b) glycidol, glycidol derivatives, or a combination of glycidol and glycidol derivatives, represented by the structure

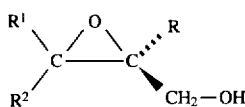

in which R, R$^1$ and R$^2$ independently can be hydrogen, C$_1$–C$_{20}$ alkyl, C$_1$–C$_5$ alkyl ether, C$_3$–C$_6$ cycloaliphatic, aromatic, or aromatic substituted with methyl, ethyl, halide, or nitro groups;

R$^1$ and R$^2$ together can be C$_5$–C$_6$ cycloaliphatic or heterocycloaliphatic with O, N, S, or P;

present in an amount of 0.9–4.0 molar equivalents per 1 mole or carboxyl groups, in the presence of (c) a carbodiimide acylating agent represented by the structure:

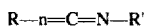

in which R and R' independently can be C$_3$–C$_{16}$ alkyl, C$_5$–C$_6$ cycloaliphatic phenyl group, or tolyl group; C$_3$–C$_{16}$ alkyl, C$_5$–C$_6$ cycloaliphatic, phenyl group, or tolyl group bound to a polymeric chain;

present in an amount of 0.9–1.1 molar equivalents per 1 mole carboxyl groups, and (d) a pyridine-type catalyst according to one of the following structures I or II:

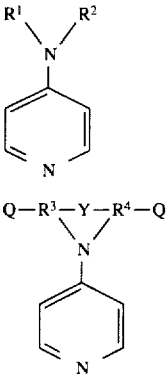

in which

R$^1$ and R$^2$ are independently C$_1$–C$_4$ alkyl,

R$^1$ and R$^2$ together are C—N—(CH$_3$)$_{2\ 2}$, cyclic (CH$_2$)$_4$, C$_2$–C$_4$ heterocycloaliphatic containing O, N, or S in any position except adjacent to the nitrogen bound to the pyridine ring, R$^3$ and R$^4$ are methine groups, Y is O, N, S, P, or C$_1$–C$_4$ alkyl, and Q is the polymerized product of vinyl comonomers or vinyl homopolymer, present in the amount of 0.10 to 5 molar equivalents based on 100 molar equivalents of carboxylic acid groups, at a temperature of 0°–15° C. until the unreacted acid content is reduced to a level represented by an acid number of 15,000 g/equivalent or greater, and B) removing any residual pyridine-type catalyst by treatment with an acidic cation exchange resin in which the pKa is equal to or less than 2.0 relative to water and in which water is present at less than 1 part by volume to 10 parts by volume of the reaction mixture.

2. The process according to claim 1 in which the carboxylic acids are selected from the group consisting of sebacic acid, stearic acid, ricinoleic acid, the dimer of oleic acid, the dimer of linoleic acid, and the dimer of tall oil fatty acid.

3. The process according to claim 1 in which the glycidol derivatives are selected from the group of racemic glycidol, 2-methylglycidol and 3-phenylglycidol.

4. The process according to claim 1 in which the carbodiimide acylating agents are 1,3-diisopropyl carbodiimide; 1,3-dicyclohexylcarbodiimide; and 2,2',6,6'-tetraisopropyldiphenyl carbodiimide.

5. The process according to claim 1 in which the pyridine-type catalyst is selected from the group consisting of the 4-di-(C$_1$–C$_4$) alkylaminopyridines.

6. The process according to claim 1 in which the pyridine-type catalyst is 4-dimethylaminopyridine.

\* \* \* \* \*